United States Patent [19]

Gleason et al.

[11] Patent Number: 4,871,771
[45] Date of Patent: Oct. 3, 1989

[54] LEUKOTRIENE ANTAGONISTS

[75] Inventors: John G. Gleason, Downingtown; Sylvia T. Hoffstein, Haverford; Charles M. Kinzig, Merion Station; Seymour Mong, Wayne; Henry M. Sarau, Harleysville, all of Pa.

[73] Assignee: SmithKline Beckman Corporation, Philadelphia, Pa.

[21] Appl. No.: 152,191

[22] Filed: Feb. 4, 1988

[51] Int. Cl.$^4$ .............................................. A61K 31/19
[52] U.S. Cl. ..................................... 514/570; 514/574
[58] Field of Search ........................ 514/438, 570, 574

[56] References Cited

U.S. PATENT DOCUMENTS

| | | | |
|---|---|---|---|
| 3,078,290 | 2/1963 | Hechenbleikner | 252/429.7 |
| 4,111,873 | 9/1978 | Cordes, III | 260/23 |
| 4,134,879 | 1/1979 | Schmidt | 260/45.85 P |
| 4,269,731 | 5/1981 | Mack | 252/400 R |
| 4,348,383 | 9/1982 | Bouillon et al. | 514/570 |
| 4,730,005 | 3/1988 | Gleason et al. | 514/438 |

FOREIGN PATENT DOCUMENTS 168902  1/1988  European Pat. Off. .
94613   3/1978  Japan .

OTHER PUBLICATIONS

Chemical Abstracts 89: 130417q (1978).
Chemical Abstracts 85: 32190h (1976).
Chemical Abstracts 71: 74808g (1969).
Perchonock et al. *Journal of Medicinal Chemistry*, 28, 1145 (1985).
Perchonock et al. *Journal of Medicinal Chemistry*, 29, 1442 (1986).
Newton et al. *Drug Metabolism and Disposition*, 15, 2, 168 (1987).
Newton et al. *Drug Metabolism and Disposition*, 15, 2, 161 (1987).

*Primary Examiner*—Douglas W. Robinson
*Assistant Examiner*—Zohreh A. Fay
*Attorney, Agent, or Firm*—Nancy S. Mayer; Janice E. Williams; Alan D. Lourie

[57] ABSTRACT

A method for inhibiting the effects of $LTB_4$ comprises administration of an effective amount of a compound represented by the following structural formula (I)

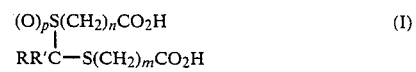

wherein m is 1 or 2; n is 1, 2 or 3; p is 0, 1, or 2; R' is hydrogen or methyl; R is phenyl substituted with A, $R_1$ and $R_2$ wherein $R_1$ and $R_2$ are independently selected from either (1) $(S)_a$—$(CH_2)_b$—$(T)_c$—B wherein a is 0 or 1; b is 5 to 12; c is 0 or 1; S and T are independently sulfur, oxygen, or $CH_2$ with the proviso that S or T are not sulfur when p is 1 or 2; and B is $C_{1-4}$alkyl, ethynyl, trifluoromethyl, or phenyl optionally monosubstituted with Br, Cl, $CF_3$, $C_{1-4}$alkoxy, $C_{1-4}$alkyl, methylthio, or trifluoromethylthio; or (2) hydrogen bromo, chloro, methyl, trifluoromethyl, methoxy or nitro; and A is selected from (2) as defined above or a pharmaceutically acceptable salt thereof. Such methods are useful in the treatment of diseases in which $LTB_4$ is a factor.

16 Claims, No Drawings

LEUKOTRIENE ANTAGONISTS

BACKGROUND OF THE INVENTION

Leukotrienes are formed by transformation of arachidonic acid into an unstable epoxide intermediate, leukotriene A4, which can be converted enzymatically by hydration to leukotriene B4 (LTB4), the structural formulae of which are represented below.

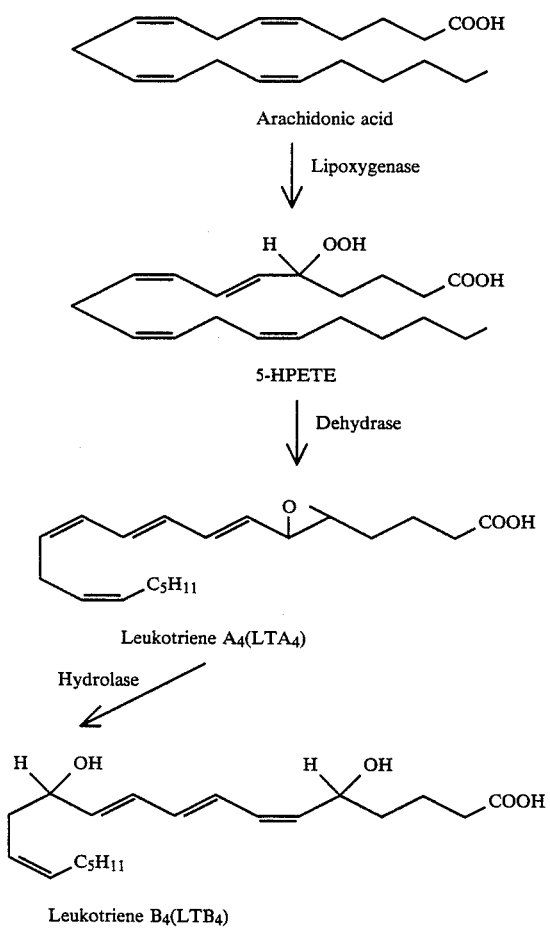

Recent literature suggests that LTB4 may play an important role in a variety of immunological diseases. LTB4 in vitro, is a mediator of leukocyte chemotaxis, chemokinesis, aggregation, degranulation, and superoxide generation. Administration of LTB4 induces inflammatory responses, i.e. PMN accumulation, increased vascular permeability, edema formation and hyperalgesia. LTB4 may also act synergistically with prostaglandins and other inflammatory mediators to exacerbate inflammatory, diseases. In addition, LTB4 has been detected in high concentrations in the inflammatory site in animal models and in inflammatory lesions in humans. Thus, LTB4 is thought to be a critical mediator of inflammatory, immediate hypersensitivity, renal, cardiovascular, and anphylactoid diseases and may possibly be involved in arthritis and other delayed type hypersensitivity diseases. Agents that interfere with the actions of LTB4, by blocking its action at the receptor, may have valuable therapeutic effects in treating these diseases.

By antagonizing the effects of LTB4, the compounds and pharmaceutical compositions useful in the instant invention are valuable in the reatment of diseases in which LTB4 is a factor.

SUMMARY OF THE INVENTION

This invention relates to methods for inhibiting the effects of LTB4 comprising administration of a compound of formula (I) or a pharmaceutical composition containing a compound of Formula (I) to a subject, human or animal, in need thereof. Such methods are useful in the treatment of diseases in which LTB4 is a factor such as immunological diseases, in particular inflammatory hypersensitivity, renal, cardiovascular, and anaphylactoid diseases.

The method of this invention for inhibiting the effects of LTB4 comprises administration of an effective amount of compounds represented by the following general structural formula (I)

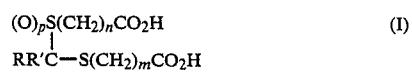

wherein m is 1, 2 or 3; n is 1, 2 or 3; p is 0, 1 or 2; R' is hydrogen or methyl; R is

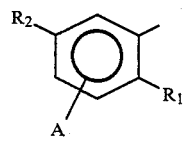

wherein $R_1$ is $(S)_a$—$(CH_2)_b$—$(T)_c$—B;

a is 0 or 1;

b is 5 to 12;

c is 0 or 1;

S and T are independently sulfur, oxygen, or $CH_2$ with the proviso that S or T are not sulfur when p is 1 or 2; and B is $C_{1-4}$alkyl, ethynyl, trifluoromethyl, or phenyl optionally monosubstituted with Br, Cl, F, $CF_3$, $C_{1-4}$alkoxy, $C_{1-4}$alkyl, methylthio, or trifluoromethylthio;

$R_2$ and A are independently selected from hydrogen, bromo, chloro, methyl, trifluoromethyl, hydroxy, methoxy or nitro; or $R_1$ is hydrogen and $R_2$ is $(S)_a$—$(CH_2)_b$—$(T)_c$—B wherein a, b, c, S, T, and B are as defined above;

or pharmaceutically acceptable salts thereof.

DETAILED DESCRIPTION OF THE INVENTION

The method of this invention comprises inhibiting the effects of LTB4 by administration of compounds represented by the following general structural formula (I)

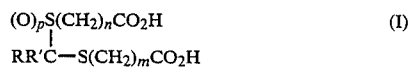

wherein m is 1, 2 or 3; n is 1, 2 or 3; p is 0, 1 or 2; R' is hydrogen or methyl; R is

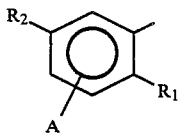

wherein
$R_1$ is $(S)_a$—$(CH_2)_b$—$(T)_c$—B;
a is 0 or 1;
b is 5 to 12;
c is 0 or 1;
S and T are independently sulfur, oxygen, or $CH_2$ with the proviso that S or T are not sulfur when p is 1 or 2; and
B is $C_{1-4}$ alkyl, ethynyl, trifluoromethyl, or phenyl optionally monosubstituted with Br, Cl, F, $CF_3$, $C_{1-4}$ alkyl, methylthio, or trifluoromethylthio;
$R_2$ and A are independently selected from hydrogen, bromo, chloro, methyl, trifluoromethyl, hydroxy, methoxy or nitro; or
$R_1$ is hydrogen and
$R_2$ is $(S)_a$—$(CH_2)_b$—$(T)_c$—B wherein a, b, c, S, T, and B are as defined above;
or pharmaceutically acceptable salts thereof.

A particular class of compounds useful in this invention are the substituted phenyldioic acid analogs of formula (I) wherein R' is hydrogen and R is the phenyl radical and are represented by the structural formula (II)

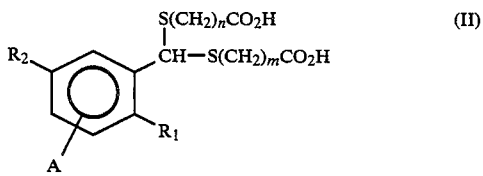

wherein m, n, $R_1$ and $R_2$ and A are described above in Formula (I).

A subgeneric class of these compounds useful in the claimed invention are the 4,6-dithianonanedioic acid derivatives represented by the following general structural formula (III)

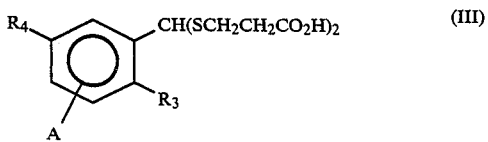

wherein $R_3$ is selected from the group consisting of $(S)_a$—$(CH_2)_b$—$(T)_c$—B wherein
a is 0 or 1;
b is 5 to 12;
c is 0 or 1;
S and T are independently sulfur, oxygen, or $CH_2$; and
B is $C_{1-4}$ alkyl, ethynyl, trifluoromethyl, or phenyl optionally monosubstituted with Br, Cl, $CF_3$, F, $C_{1-4}$alkoxy, $C_{1-4}$alkyl, methylthio, or trifluoromethylthio; and
$R_4$ and A are independently selected from hydrogen, bromo, chloro, methyl, trifluoro-methyl, hydroxy, methoxy or nitro.

The compounds of the formula (III) wherein $R_4$ is hydrogen are exemplified by the following classes of compounds:

(A) where $R_3$ is an alkyl radical containing from 8 to 13 carbon atoms:
(1) 4,6-dithia-5-(2-dodecylphenyl)nonanedioic acid;
(2) 4,6-dithia-5-(2-decylphenyl)nonanedioic acid; and
(3) 4,6-dithia-5-(2-octylphenyl)nonanedioic acid;

(B) where $R_3$ is an alkoxy radical containing from 7 to 12 carbon atoms:
(1) 4,6-dithia-5-(2-undecyloxyphenyl)nonanedioic acid; and
(2) 4,6-dithia-5-(2-nonyloxyphenyl)nonanedioic acid;

(C) where $R_3$ is an alkylthio radical containing from 7 to 12 carbon atoms or a 1-alkynyl radical containing from 10 to 12 carbon atoms:
(1) 4,6-dithia-5-(2-undecylthiophenyl)nonanedioic acid; and
(2) 4,6-dithia-5-[2-(1-dodecyn-1-yl)phenyl]nonanedioic acid;

(D) where $R_3$ is an 2,5-undecadienyloxy radical:
4,6-dithia-5-[2-(2,5-undecadienyloxy)phenyl]nonanedioic acid;

(E) where $R_3$ is a phenyl-$C_4$ to $C_{10}$ alkyl radical (optionally substituted), phenylthio-$C_3$ to $C_9$ alkyl radical (optionally substituted), or phenyl-$C_3$ to $C_9$ alkoxy radical;
(1) 4,6-dithia-5-[2-(8-phenyloctyl)phenyl]nonanedioic acid;
(2) 4,6-dithio-5-[2-(6-phenylhexyloxy)phenyl]nonanedioic acid;
(3) 4,6-dithia-5-[2-(8-(4-trifluoromethylphenyl)octyl)-phenyl]nonanedioic acid; and
(4) 4,6-dithia-5-[2-(7-phenylthioheptyl)phenyl]-nonanedioic acid; and (F) where $R_3$ is a trifluoromethyl-$C_7$ to $C_{12}$ alkyl radical;
4,6-dithia-5-[2-(12,12,12-trifluorododecyl)phenyl]-nonanedioic acid.

The compounds of the formula (III) wherein $R_4$ is bromo, chloro, methyl, trifluoromethyl, hydroxy, methoxy or nitro are exemplified by the following compounds:
(A) 4,6-dithia-5-(5-methoxy-2-undecyloxyphenyl)-nonanedioic acid;
(B) 4,6-dithia-5-(5-bromo-2-undecyloxyphenyl)-nonanedioic acid;
(C) 4,6-dithia-5-(5-nitro-2-undecyloxyphenyl)nonanedioic acid;
(D) 4,6-dithia-5-(5-hydroxy-2-undecyloxyphenyl)-nonanedioic acid; and
(E) 4,6-dithia-5-[2-(8-phenyloctyl)-5-trifluoromethylphenyl]nonanedioic acid.

An additional subgeneric class of the compounds of Formula (II) are the 4,6-dithianonanedioic acid derivatives represented by the following general structural formula (IV)

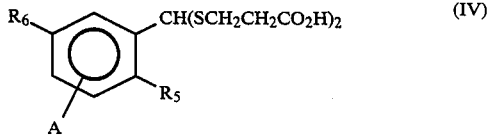

wherein $R_6$ is selected from the group consisting of $(S)_a$—$(CH_2)_b$—$(T)_c$—B wherein
a is 0 or 1;

b is 5 to 12;

c is 0 or 1;

S and T are independently sulfur, oxygen, or $CH_2$;

B is $C_{1-4}$ alkyl, ethynyl, trifluoromethyl, or phenyl optionally monosubstituted with Br, Cl, $CF_3$, $C_{1-4}$ alkoxy, $C_{1-4}$ alkyl, methylthio, or trifluoromethylthio and $R_5$ and A are independently selected from hydrogen, bromo, chloro, methyl, trifluoromethyl, hydroxy, methoxy, or nitro.

The compounds of formula (IV) useful in the method of the present invention wherein $R_5$ is hydrogen are exemplified by the following compounds in which $R_6$ is an alkoxy radical containing from 7 to 12 carbon atoms:

(A) 4,6-dithia-5-(3-undecyloxyphenyl)nonanedioic acid; and (B) 4,6-dithia-5-(3-nonyloxyphenyl)nonanedioic acid.

The compounds of the formula (IV) are also exemplified by 4,6-dithia-5-[3-(2,5-undecadienyloxy)phenyl]-nonanedioic acid and 4,6-dithia-5-[3-(8-phenyloctyl)-phenyl]nonanedioic acid.

Additional subgeneric classes of the compounds of Formula (II) are the 3,5-dithiaheptanedioic acid derivatives where both m and n are 1; 4,6-dithiadecanedioic acid derivatives where m is 2 and n is 3; and the 3,5-dithiaoctanedioic acid derivatives where m is 1 and n is 2. The 3,5-dithiaheptanedioic acid derivatives of formula (II) are exemplified by 3,5-diathia-4-(2-dodecylphenyl)heptanedioic acid.

A further class of compounds useful in the method of this invention are the compounds of the formula (I) wherein p is 1. Exemplifying this class of compounds is 5-(2-dodecylphenyl)-4-sulfinyl-6-thianonanedioic acid [formula I wherein m and n are both 2, R' is hydrogen, R is 2-dodecylphenyl and p is 1].

The compounds useful in the method of the present invention are acidic and are, therefore, capable of forming salts with pharmaceutically acceptable bases according to procedures well known in the art. Such acceptable bases include organic and inorganic bases, such as ammonia, organic amines and alkali metal bases.

The compounds of the formula (I) wherein p is 0 are conveniently prepared by forming the dithioacetal derivatives or dithioketal derivatives of aldehydes or ketones, utilizing the appropriate mercaptoalkanoic acids. The reaction of the aldehyde or ketone with two equivalents or an excess of the mercaptoalkanoic acid is accomplished at low to moderate temperatures under acidic conditions in an inert solvent. Examples of such inert solvents include chlorinated hydrocarbons, such as methylene chloride, chloroform and dichloroethane. The acidic conditions are produced by mineral acids, such as hydrochloric acid and sulfuric acid, or Lewis acids, such as boron trifluoride etherate. The reaction temperatures can range from $-40°$ C. to ambient temperatures.

The compounds of the formulae (III) and (IV) are prepared by reacting 3-mercapto-propionic acid with the appropriate aldehyde. Similarly, employing mercaptoacetic acid, the compounds of the formula (I) wherein both m and n are 1 and p is 0 can be prepared. To prepare the compounds of formula (I) wherein m is not equal to n and p is 0, a mixture of the appropriate mercaptoalkanoic acids is employed followed by separation and isolation of the desired compounds.

To prepare the compounds of formula (I) wherein p is 1, the appropriate dithia acid product is conveniently oxidized with either metachloroperbenzoic acid or, when $R_1$ or $R_2$ contains unsaturation, sodium periodate, using one equivalent of either oxidant.

The aldehydes and ketones used above are known or readily prepared utilizing the general procedures described as follows.

The aldehyde precursors to the compounds of the formula (II) wherein $R_1$ is, for example, an alkyl radical containing 8 to 13 carbon atoms are prepared from the appropriate 2-methoxyphenyl-4,4-dimethyloxazoline [see Meyers et al. *J. Org. Chem.*, 43 1372 (1978)].

The aldehyde precursors of the compounds of the formula (II) wherein $R_1$ or $R_2$ is, for example, an alkoxy radical containing 7 to 12 carbon atoms or a 2(Z),5(Z)-undecadienyloxy radical are prepared by the O-alkylation of the appropriate 2 or 3 hydroxybenzaldehyde with the corresponding alkylating agent.

The aldehyde precursors to the compounds of the formula (II) wherein $R_1$ or $R_2$ is a 1-alkynyl radical containing 10 to 12 carbon atoms are prepared by coupling a 2 or 3 substituted halobenzaldehyde with the appropriate 1-alkyne in the presence of cuprous iodide and $(Ph_3P)_2PdCl_2$. [See Hagihara, et al. *Synthesis*, 627, (1980)]. The catalytic hydrogenation of these alkynyl containing precursors under standard conditions affords the aldehyde precursors of the compounds of the formula (II) wherein $R_1$ or $R_2$ is an alkyl or phenylalkyl radical.

The alkylthio containing aldehyde precursors of the compounds of the formula (II) are prepared by the reaction of the appropriately substituted halothioalkylbenzene with magnesium and dimethylformamide.

The phenylthioalkyl containing aldehyde precursors of the compounds of the formula (II) are prepared by the reaction of the appropriately substituted haloalkyl benzoic acid with a thiophenol and triethylamine, followed by reduction with lithium aluminum hydride to the benzyl alcohol and oxidation with manganese dioxide to the desired aldehyde.

The receptor binding affinity of the compounds used in the method of this invention is measured by the the ability of the compounds to bind to [$^3$H]-LTB$_4$ binding sites on human U937 cell membranes. The LTB$_4$ antagonist activity of the compounds used in the method of this invention is measured by their ability to antagonize in a dose dependent manner the LTB$_4$ elicited calcium transient measured with fura-2, the fluorescent calcium probe. The methods employed were as follows.

U937 Cell Culture Conditions

U937 cells were obtained from Dr. John Bomalaski (Medical College of PA) and Dr. John Lee (SK&F, Dept. of Immunology) and grown in RPMI-1640 medium supplemented with 10% (v/v) heat inactivated fetal calf serum, in a humidified environment of 5% $CO_2$, 95% air at 37° C. Cells were grown both in T-flasks and in Spinner culture. For differentiation of the U937 cells with DMSO to monocyte-like cells, the cells were seeded at a concentration of $1 \times 10^5$ cells/ml in the above medium with 1.3% DMSO and incubation continued for 4 days. The cells were generally at a density of $0.75-1.25 \times 10^6$ cells/ml and were harvested by centrifugation at $800 \times g$ for 10 min.

Preparation of U937 Cell Membrane Enriched Fraction

Harvested U937 cells were washed with 50 mM Tris-HCl, pH 7.4@25° containing 1 mM EDTA (buffer A). Cells were resuspended in buffer A at a concentration of $5 \times 10^7$ cells/ml and disrupted by nitrogen cavitation with a Parr bomb at 750 psi for 10 min@0° C. The broken cell preparation was centrifuged at 1,000×g for 10 min. The supernatant was centrifuged at 50,000×g for 30 min. The pellet was washed twice with buffer A. The pellet was resuspended at about 3 mg membrane protein/ml with 50 mM Tris HCl, pH 7.4 at 25° and aliquots were rapidly frozen and stored at −70°.

Binding of [$^3$H]-LTB$_4$ to U937 Membrane Receptors

[$^3$H]-LTB$_4$ binding assays were performed at 25° C. in 50 mM Tris-HCl (pH 7.5) buffer containing 10 mM CaCl$_2$, 10 mM MgCl$_2$, [$^3$H]-LTB$_4$, U937 cell membrane protein (standard conditions) in the presence (or absence of varying concentrations of LTB$_4$ or SK&F compounds. Each experimental point represents the means of triplicate determinations. Total and non-specific binding of [$^3$H]-LTB$_4$ were determined in the absence or presence of 2 μM of unlabeled LTB$_4$, respectively. Specific binding was calculated as the difference between total and non-specific binding. The radioligand competition experiments were performed, under standard conditions, using approximately 0.2 nM [$^3$H]-LTB$_4$, 20–40 μg of U937 cell membrane protein, increasing concentrations of LTB$_4$ (0.1 nM to 10 nM) or other competing ligands (0.1 μM to 30 μM) in a reaction volume of 0.2 ml and incubated for 30 minutes at 25°. The unbound radioligand and competing drugs were separated from the membrane bound ligand by a vacuum filtration technique. The membrance bound radioactivity on the filters was determined by liquid scintillation spectrometry.

Saturation binding experiments for U937 cells were performed, under standard conditions, using approximately 15–50 μg of U937 membrane protein and increasing concentrations of $^3$H]-LTB$_4$ (0.02–2.0 mM) in a reaction volume of 0.2 ml and incubation at 22° C. for 30 minutes. LTB$_4$ (2 μM) was included in a separate set of incubation tubes to determine non-specific binding. The data from the saturation binding experiments was subjected to computer assisted non-linear least square curve fitting analysis and further analyzed by the method of Scatchard.

Uptake of Fura-2 by Differentiated U937 Cells

Harvested cells were resuspended at 2×10$^6$ cells/ml in Krebs Ringer Hensilet buffer containing 0.1% BSA (RIA grade), 1.1 mM MgSO$_4$, 1.0 mM CaCl$_2$ and 5 mM HEPES (pH 7.4, buffer B). The diacetomethoxy ester of fura-2 (fura-2/AM) was added to a final concentration of 2 uM and cells incubated in the dark for 30 minutes at 37° C. The cells were centrifuged at 800×g for 10 minutes and resuspended at 2×10$^6$ cells/ml in fresh buffer B and incubated at 37° C. for 20 minutes to allow for complete hydrolysis of entrapped ester. The cells were centrifuged at 800×g for 10 minutes and resuspended in cold fresh buffer B at 5×10$^6$ cells/ml. Cells were maintained on ice in the dark until used for fluorescent measurements.

Fluorescent Measurements—Calcium Mobilization

The fluorescence of fura-2 containing U937 cells was measured with a fluorometer designed by the Johnson Foundation Biomedical Instrumentation Group. Fluorometer is equipped with temperature control and a magnetic stirrer under the cuvette holder. The wavelengths are set at 339 nm for excitation and 499 nm for emission. All experiments were performed at 37° C. with constant mixing.

U937 cells were diluted with fresh buffer to a concentration of 1×10$^6$ cells/ml and maintained in the dark on ice. Aliquots (2 ml) of the cell suspension were put into 4 ml cuvettes and the temperature brought up to 37° C. (maintained in 37° C. water bath for 10 min). Cuvettes were transferred to the fluorometer and fluorescence measured for about one minute before addition of stimulants or antagonists and followed for about 2 minutes post stimulus. Agonists and antagonists were added as 2 ul aliquots.

Antagonists were added first to the cells in the fluorometer in order to detect potential agonist activity. Then after about one minute 10 nM LTB$_4$ (a near maximal effective concentration) was added and the maximal Ca$^{2+}$ mobilization [Ca$^{2+}$]$_i$ was calculated. [Ca$^{2+}$]$_i$ was calculated using the following formula:

$$[Ca^{2+}]_i = 224 \frac{F - F_{min}}{F_{max} - F}$$

F was the maximum relative fluorescence measurement of the sample. $F_{max}$ was determined by lysing the cells with 10 ul of 10% Triton X-100 (final Concentration 0.02%). After $F_{max}$ was determined 67 ul of 100 mM EGTA solution (pH 10) was added to totally chelate the Ca$^{2+}$ and quench the fura-2 signal and obtain the $F_{min}$. The [Ca$^{2+}$]$_i$ level for 10 nM LTB$_4$ in the absence of an antagonist was 100% and basal [Ca$^{2+}$]$_i$ was 0%. The IC$_{50}$ concentration is the concentration of antagonist which blocks 50% of the 10 nM LTB$_4$ induced [Ca$^{2+}$]$_i$ mobilization. The EC$_{50}$ for LTB$_4$ induced increase in [Ca$^{2+}$]$_i$ mobilization was the concentration for half maximal increase. The K$_i$ for calcium mobilization was determined using the formula:

$$K_i = \frac{IC_{50}}{1 + \frac{[LTB_4]}{[EC_{50}]}}$$

With the experiments described, the LTB$_4$ concentration was 10 nM and the EC$_{50}$ was 2 nM.

The compounds used in the method of the present invention show significant receptor binding affinity and LTB$_4$ antagonist activity. Data for representative compounds is shown in Table I.

TABLE I

| Structure | LTB$_4$ Binding Human U937 K$_i$ (μM) | Inhibition of LTB$_4$ Induced Ca$^{2+}$ flux K$_i$ (μM) |
|---|---|---|
| 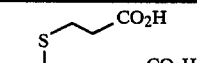 | 6.5 | |
| 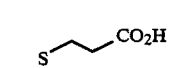 | 5.3 | |
| 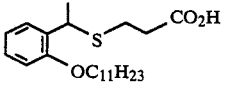 | 4.2 | 5.6 |

TABLE I-continued

| Structure | LTB$_4$ Binding Human U937 K$_i$ (μM) | Inhibition of LTB$_4$ Induced Ca$^{2+}$ flux K$_i$ (μM) |
|---|---|---|
| 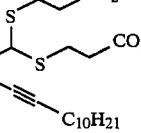 | 7 | |
| 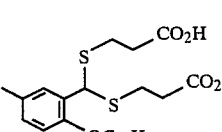 | 2.2 | 5.0 |
| 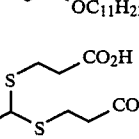 | 4.4 | 7.0 |
| 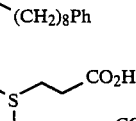 | 5.3 | |
| 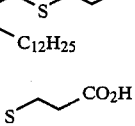 | 7.3 | |
| 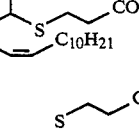 | 6 | |
| 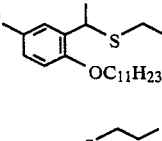 | 9.6 | |
| 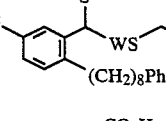 | 4.3 | |
| 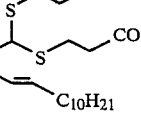 | 2.1 | 5.2 |
| 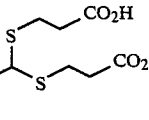 | 1.3 | 8.7 |
| (further structures) | 4.5 | |
| | 1.2 | 7.6 |
| | 11 | 4.8 |
| | 10 | |
| | 5.3 | |
| | 2.8 | 6.7 |
| | 3.3 | 6.4 |
| | | 7.8 |

Pharmaceutical compositions useful in the methods of the present invention comprise a pharmaceutical carrier or diluent and an amount of a compound of the formula (I) or a pharmaceutically acceptable salt, such as an alkali metal salt thereof, sufficient to produce the inhibition of the effects of leukotriene B$_4$.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier of diluent will, of course, depend upon the intended route of administration, i.e. suppositories, parenterally, topically, orally or by inhalation.

For administration by inhalation, the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

For topical administration the pharmaceutical composition will be in the form of a cream, ointment, or spray.

Usually a compound of Formula (I) is administered to an animal subject in a composition comprising a nontoxic amount sufficient to produce the desired effect. When employed in this manner, the dosage of the composition is selected from the range of from about 1 mg/kg to about 500 mg/kg of active ingredient for each administration, preferably from about 50 to about 100 mg/kg.

The pharmaceutical preparations thus described are made following the conventional techniques of the pharmaceutical chemist as appropriate to the desired end product.

The following examples illustrate the preparation of the compounds useful in the method of this invention and their incorporation into pharmaceutical compositions and as such are not to be considered as limiting the invention set forth in the claims appended hereto.

EXAMPLE 1

Preparation of
4,6-Dithia-5-(2-dodecylphenyl)nonanedioic acid (a) 2-(2-Dodecylphenyl)-4,4-dimethyloxazoline To freshly prepared dodecylmagnesium bromide (from 30.13 mmoles of dodecyl bromide and 26.20 mmoles of magnesium) in distilled tetrahydrofuran (50 ml) was added 2-(2-methoxyphenyl)-4,4-dimethyloxazoline [A. I. Meyers et al., *J. Org. Chem.*, 43, 1372 (1978)] (17.88 mmoles) in tetrahydrofuran (30 ml). The resultant yellow solution was stirred under argon at ambient temperature for 20 hours. The solution was cooled in an ice water bath and quenched with aqueous ammonium chloride (100 ml). The reaction product was extracted into diethyl ether (100 ml) and the organic phase was washed with saturated sodium chloride solution (50 ml) and then dried over anhydrous magnesium sulfate. Evaporation of the organic phase afforded a colorless oil which was purified by flash chromatography over silica gel with 5 percent ethyl acetate in hexane as eluant to afford the desired product as a pale yellow oil.

Analysis for $C_{23}H_{37}NO$: Calculated: C, 80.41; H, 10.85; N, 4.08. Found: C, 80.22; H, 10.56; N, 3.87.

(b) 2-(2-Dodecylphenyl)-3,4,4-trimethyloxazolinium iodide

A solution of the compound of Example 1(a) (17.2 mmoles) in methyl iodide (20 ml) was refluxed under argon for 18 hours. The volatiles were removed under vacuum and the solid residue triturated with ethyl acetate (25 ml) to afford the desired product as white crystals (mp 78°–84° C.).

(c) 2-Dodecylbenzaldehye

To an ice cold solution of the compound of Example 1(b) (10.0 mmoles) in methanol (50 ml) over a period of 15 minutes was added in small portions sodium borohydride (10.0 mmoles). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate. Evaporation of the extract afforded an oil which was dissolved in acetone (50 ml) and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil. Analysis for $C_{19}H_{30}O$: Calculated: C, 83.15; H, 11.02. Found C, 82.59; H, 10.65.

(d) 4,6-Dithia-5-(2-dodecylphenyl)nonanedioic acid

To an ice solution of the compound of Example 1(c) (4.23 mmoles) and 3-mercaptopropionic acid (9.3 mmoles) in methylene chloride (25 ml) was added dropwise distilled boron trifluoride etherate (4.23 mmoles). After 15 minutes, the mixture was taken up in diethylether (100 ml) and washed with water (5×100 ml). The organic phase was dried over anhydrous magnesium sulfate and after removal of the volatiles under vacuum, the resultant colorless oil was stored under argon in a freezer. It slowly crystallized to afford the desired product as a white solid (mp 34°–38° C.). Analysis for $C_{25}H_{40}O_4S_2$: Calculated: C, 64.06; H, 8.60; S, 13.68. Found C, 64.19; H, 8.47; S, 13.63.

The following compounds were prepared according to the general method described above from the 2-(2-methoxyphenyl)-4,4-dimethyloxazoline and the appropriate alkyl halide:

4,6-dithia-5-(2-decylphenyl)nonanedioic acid (mp 66°–69.5° C.);

4,6-dithia-5-(2-octylphenyl)nonanedioic acid (mp 61°–64° C.); and 3,5-dithia-4-(2-dodecylphenyl)heptanedioic acid (mp 80°–81.5° C.).

Similarly, the following compounds of the formula (II) are prepared utilizing the general method of Example 1 from the appropriate reactants:

| m | n | $R_1$ | $R_2$ |
|---|---|-------|-------|
| 1 | 1 | $C_{10}H_{21}$ | Br |
| 1 | 1 | $C_8H_{17}$ | $OCH_3$ |

EXAMPLE 2

Preparation of
4,6-Dithia-5-(2-undecyloxyphenyl)nonanedioic acid (a) 2-undecyloxybenzaldehyde To a stirred suspension of sodium hydride (10.0 mmoles), which was prewashed with petroleum ether, in sieve dried dimethylformamide (10 ml) was added dropwise a solution of salicylaldehyde (10.1 mmoles) in dimethylformamide (1 ml). To the reaction mixture was then added undecyl bromide (10.0 mmoles) and the mixture stirred for 16 hours at ambient temperature under nitrogen. The reaction mixture was taken up in hexane (50 ml) and washed with 10 percent sodium hydroxide (2×50 ml) and saturated sodium chloride (50 ml). The organic phase was dried over anhydrous magnesium sulfate and charcoal. Evaporation of the volatiles yielded a colorless liquid which was purified by flash chromatography over silica gel with 2 percent ethyl acetate in hexane as eluant to afford the desired product as an oil.

Analysis for $C_{18}H_{28}O_2$: Calculated: C, 78.21; H, 10.21. Found: C, 77.92; H, 9.95.

(b) 4,6-Dithia-5-(2-undecyloxyphenyl)nonanedioic acid

Employing the general method of Example 1(d), the compound of Example 2(a) (3.62 mmoles) was reacted with 3-mercaptopropionic acid (8.03 mmoles) to yield the desired product as a white crystalline solid (mp 76°–78.5° C.).

Analysis for $C_{24}H_{38}O_5S_2$: Calculated: C, 61.24; H, 8.14; S, 13.62. Found: C, 61.56; H, 8.08; S, 13.51.

The following compounds were prepared according to the general method described above from the appropriately substituted hydroxybenzaldehyde and the appropriate alkyl halide.

4,6-dithia-5-(2-nonyloxyphenyl)nonanedioic acid (mp. 76°–78.5° C.);

4,6-dithia-5[2-(2(Z),5(Z)-undecadienyloxy)phenyl]nonanedioic acid (oil);

4,6-dithia-5-(5-methoxy-2-undecyloxyphenyl)nonanedioic acid (mp 55°–57° C.);

4,6-dithia-5-(5-bromo-2-undecyloxyphenyl)nonanedioic acid (mp 79°–81° C.);

4,6-dithia-5-(5-nitro-2-undecyloxyphenyl)nonanedioic acid (mp 99°–101° C.);

4,6-dithia-5-(5-hydroxy-2-undecyloxyphenyl)nonanedioic acid (mp 102°–105° C.);

4,6-dithia-5-(3-undecyloxyphenyl)nonanedioic acid (mp 59°–60.5° C.);

4,6-dithia-5-(3-nonyloxyphenyl)nonanedioic acid (mp 78°–79° C.) and 4,6-dithia-5-[3-(2(Z),5(Z)-undecadienyloxy)phenyl]-nonanedioic acid (oil).

4,6-Dithia-5-(2-undecylthiophenyl)nonanedioic acid [formula (III) where $R_3$ is $-SC_{11}H_{23}$ and $R_4$ is H] was prepared from 2-(undecylthio)benzaldehyde and was obtained in the form of an oil.

Analysis for $C_{24}H_{38}O_4S_3$: Calculated: C, 59.22; H, 7.87; S, 19.76. Found: C, 58.90, H, 7.91; S, 19.06, 18.92.

The following compound of the formula (I) wherein R' is methyl was prepared according to the general method described above from the appropriate substituted alkoxyacetophenone:

4,6-dithia-5-methyl-5-(2-undecyloxyphenyl)nonanedioic acid (amorphous solid).

Analysis for $C_{25}H_{40}O_5S_2$: Calculated: C, 61.95; H, 8.32. Found: C, 61.15; H, 8.22.

Similarly, the following compounds of the formula (II) are prepared utilizing the general method of Example 2 from the appropriate reactants.

| m | n | $R_1$ | $R_2$ |
|---|---|-------|-------|
| 1 | 1 | $OC_{11}H_{23}$ | H |
| 1 | 1 | $OC_9H_{19}$ | Br |
| 1 | 1 | H | $OC_{11}H_{23}$ |

EXAMPLE 3

Alternate Preparation of Alkoxybenzaldehyde Intermediates (a) 2-Undecyloxybenzaldehyde A mixture of salicylaldehyde (10.15 moles), undecylbromide (10.3 mmoles) and potassium carbonate (11.7 mmoles) in dimethylformamide (10 ml) is heated to 100° C. for 1 hour and then is cooled. The reaction mixture is taken up in hexane and is washed with 5 percent sodium hydroxide and brine. After treatment with anhydrous magnesium sulfate and charcoal, the volatiles are removed under vacuum and the residue is purified by flash chromatography to give the desired product.

EXAMPLE 4

Preparation of
4,6-Dithia-5-[2-(1-dodecyn-1-yl)phenyl]nonanedioic acid (a) 2-(1-dodecyn-1-yl)benzaldehyde A mixture of 2-bromobenzaldehyde (10.05 mmoles), 1-dodecyne (12.03 mmoles), cuprous iodide (0.11 mmoles) and bis(triphenylphosphine) palladium chloride (0.20 mmoles) in freshly distilled triethylamine (30 ml.) was heated for one hour at reflux producing a white precipitate. The reaction mixture was cooled and filtered. The filtrate was evaporated to dryness at reduced pressure and then dissolved in diethyl ether (50 ml) and washed with brine (50 ml). After treatment with anhydrous magnesium sulfate and charcoal, the solution was evaporated to afford a dark oil, which was purified by flash chromatography (2% $Et_2O$/hexane) to yield the desired product.

(b) 4,6-Dithia-5-[2-(1-dodecyn-1-yl)phenyl]nonanedioic acid

Employing the general method of Example 1(d), the compound of Example 4(a) (2.26 mmoles) was reacted with mercaptopropionic acid (4.93 mmoles) to yield the desired product as a pale yellow liquid.

Analysis for $C_{25}H_{36}O_4S_2$: Calculated: C, 64.62; H, 7.81; S, 13.80. Found: C, 63.90; H, 7.72; S, 13.76.

EXAMPLE 5

Preparation of 4,6-Dithia-5-[2-(6-phenylhexyloxy)phenyl]nonanedioic acid (a) 2-(6-Phenylhexyloxy)benzaldehyde A solution of 6-phenylhexanoic acid (19.8 mmoles) in sieve dried tetrahydrofuran (5 ml) was reduced with diborane in tetrahydrofuran (30 ml, 29.1 mmoles) at 0° C. for 4 hours to give 6-phenylhexanol. To an ice cold solution of the hexanol (ca. 19.8 mmoles) and carbon tetrabromide (21.98 mmoles) in methylene chloride (50 ml) was added triphenylphosphine (22.30 mmoles) in methylene chloride (50 ml) and the resulting solution was stirred for 2.5 hours. The volatiles were evaporated and the residue was taken up in ether (100 ml), cooled in ice, and filtered. The filtrate was evaporated and distilled to afford 6-phenylhexyl bromide as an oil. A mixture of the bromide (8.00 mmoles), salicylaldehyde (8.19 mmoles) and potassium carbonate (9.33 mmoles) in dimethylformamide (10 ml) was heated to 100° C. and maintained at that temperature for one hour. The cooled reaction mixture was taken up in hexane (50 ml) and washed with 5% sodium hydroxide (50 ml) and saturated sodium chloride (50 ml). The organic phase was dried over anhydrous magnesium sulfate and charcoal. Evaporation yielded a colorless oil which was purified by flash chromatography over silica gel with 5% ethyl acetate in hexane as eluant to afford the desired product as an oil.

Analysis for $C_{19}H_{22}O_2$: Calculated: C, 80.82; H, 7.85. Found: C, 80.62; H, 7.72.

(b) 4,6-Dithia-5-[2-(6-phenylhexyloxy)phenyl]nonanedioic acid

Employing the general method of Example 1(d), the compound of Example 5(a) (5.35 mmoles) was reacted with 3-mercaptopropionic acid (11.47 mmoles) to yield the desired product as a white solid (mp 71°–74° C.).

Analysis for $C_{25}H_{32}O_5S_2$: Calculated: C, 63.00; H, 6.77; S, 13.45. Found: C, 62.88; H, 6.74; S, 13.40.

EXAMPLE 6

Preparation of 4,6-Dithia-B 5-[2-(8-phenyloctyl)phenyl]nonanedioic acid (a) 2-(8-Phenyloctyl)benzaldehyde Following the procedures of Example 1(a), (b) and (c), to 8-phenyloctylmagnesium bromide (from 24.25 mmoles of 8-phenyloctyl bromide and 21.27 mmoles of magnesium) in distilled tetrahydrofuran (40 ml) was added 2-(2-methoxyphenyl)-4,4-dimethyloxazoline (17.10 mmoles) in tetrahydrofuran (20 ml). [The 8-phenyloctyl bromide was prepared from 8-phenyloctanol, carbon tetrabromide and triphenylphosphine in methylene chloride as described in Example 5(a).] After stirring for 24 hours, the reaction mixture was similarly worked up to yield 2-[2-(8-phenyloctyl)phenyl]-4,4-dimethyloxazoline as an oil. A solution of the oxazoline (11.58 mmoles) in methyl iodide (20 ml) was refluxed under argon for 18 hours. Removal of the volatiles afforded the corresponding 3,4,4-trimethyloxazolinium iodide as a white solid (mp 76.5°–78° C.). To an ice cold solution of the iodide (9.46 mmoles) in methanol (35 ml) was added in portions sodium borohydride (9.20 mmoles). Treatment of the reaction mixture as in Example 1(c) results in the isolation of the desired product as an oil.

Analysis for $C_{21}H_{26}O$: Calculated: C, 85.67; H, 8.90. Found: C, 85.12, 85.22; H, 8.94, 8.96.

(b) Alternative preparation of 2-(8-phenyloctyl)benzaldehyde

A solution of 5-hexynyl alcohol (102 mmoles) in pyridine (150 ml), under argon, was cooled to 0° C. and p-toluenesulfonyl chloride (204 mmoles) was added. The reaction mixture was kept at about 4° C. for 18 hours, poured into ice-water and then taken up in ether. The ether extract was washed with cold 10% hydrochloric acid, water and brine. The organic layer was dried and concentrated in vacuo to give 5-hexynyl p-toluenesulfonate. A solution of phenylacetylene (97 mmoles) in tetrahydrofuran (200 ml) containing a trace of triphenylmethane was cooled to 0° C. and then n-butyl lithium (37.3 ml of 2.6 molar in hexane) was added dropwise. The resulting solution was stirred at 0° C. for 10 minutes and hexamethylphosphoramide (21 ml) was added dropwise. After stirring for 10 minutes a solution of 5-hexynyl p-toluenesulfonate (97.1 mmoles) in tetrahydrofuran (200 ml) was added. The reaction mixture was stirred for 18 hours, diluted with ether and the organic layer was washed with water and brine. The dried organic solution was concentrated and the product was purified by flash chromatography to give 1-phenylocta-1,7-diyne. A mixture of this compound (43 mmoles), 2-bromobenzaldehyde (35.8 mmoles), cuprous iodide (0.5 mmoles) and bis(triphenylphosphine) palladium chloride (0.7 mmoles) in triethylamine (100 ml) was heated in an oil bath (95° C.) for one hour. The reaction mixture was cooled to 0° C., filtered and the filtrate was concentrated. The residue was dissolved in ether, washed with 10% hydrochloric acid, water and brine. The organic layer was dried and concentrated to give a product which was purified by flash chromatography to yield 2-(8-phenylocta-1,7-(diene)benzaldehyde. A solution of this compound (24.1 mmoles) in ethyl acetate (100 ml) and 10% palladium on charcoal (1 g) was hydrogenated (40 psi of hydrogen) at room temperature for 15 minutes. The catalyst was filtered off and the filtrate concentrated to give the 2-(8-phenyloctyl)benzaldehyde.

(c) 4,6-Dithia-5-[2-(8-phenyloctyl)phenyl]nonanedioic acid

To an ice cold solution of the aldehyde from Example 6(a) or 6(b) (5.94 mmoles) and 3-mercaptopropionic acid (12.97 mmoles) in methylene chloride (32 ml) was added dropwise boron trifluoride etherate (5.94 mmoles). After 15 minutes the reaction mixture was diluted with ether (100 ml) and washed with water (5×100 ml). The organic phase was dried over anhydrous magnesium sulfate and charcoal. Evaporation of the volatiles yielded an oil which crystallized to the desired product as a white solid (mp 56°–59° C.).

Analysis for $C_{27}H_{36}O_4S_2$: Calculated: C, 66.36; H, 7.42; S, 13.12. Found: C, 66.16; H, 7.34; S, 13.16.

EXAMPLE 7

Preparation of 4,6-Dithia-5-[2-(12,12,12-trifluorododecyl)-phenyl]-nonanedioic acid

(a) 2-(12,12,12-trifluorododecyl)benzaldehyde

Following the procedures of Example 1(a), (b) and (c), 12,12,12-trifluorododecylmagnesium bromide (from 29.19 mmoles of 12,12,12-trifluorododecyl bromide and 25.71 mmoles of magnesium) was reacted with 2-(2-methoxyphenyl)-4,4-dimethyloxazoline (20.17 mmoles) in tetrahydrofuran to give 2-[2-(12,12,12-trifluorododecyl)phenyl]-4,4-dimethyloxazoline. The oxazoline (14.39 mmoles) was converted to the methiodide salt and then reduced with sodium borohydride (13.43 mmoles) to yield the desired product as an oil.

Analysis for $C_{19}H_{27}F_3O$: Calculated: C, 69.49; H, 8.29. Found: C, 69.04, 69.14; H, 8.26, 8.31.

[12,12,12-Trifluorododecyl bromide was obtained by reaction of 12-bromododecanoic acid with an excess of sulfur tetrafluoride under pressure at 125° C. for 10 hours.]

(b) 4,6-Dithia-5-[2-(12,12,12-trifluorododecyl)phenyl]-nonanedioic acid

To an ice cold solution of the aldehyde from Example 7(a) (8.65 mmoles) and 3-mercaptopropionic acid (18.93 mmoles) in methylene chloride (40 ml) was added dropwise boron trifluoride etherate (8.62 mmoles). After 15 minutes the reaction mixture was taken up in ether (150 ml) and washed with water (5×150 ml). The organic phase was dried over anhydrous magnesium sulfate and charcoal, then evaporated to leave an oil which crystallized on cooling to give the desired product as a white solid. Purification by flash chromatography over silica gel with hexane/ethyl acetate/formic acid as eluant afforded the purified product (mp 42°–44.5° C.).

Analysis for $C_{25}H_{37}F_3O_4S_2$: Calculated: C, 57.45; H, 7.13; S, 12.27. Found: C, 57,54; H, 7.07; S, 12.24.

EXAMPLE 8

Preparation of 5-(2-Dodecylphenyl)-4-sulfinyl-6-thianonanedioic acid

A solution of metachloroperbenzoic acid (2.81 mmoles) in methylene chloride (25 ml) was added dropwise over 15 minutes to an ice cold solution of 4,6-dithia-5-(2-dodecylphenyl)nonanedioic acid (2.82 mmoles), prepared as in Example 1(d), in methylene chloride (25 ml). The solution was stirred at 0° C. for 45 minutes, the volatiles were removed by evaporation and the solid residue purified by flash chromatography over silica gel using ethyl acetate/hexane/formic acid as eluant to give the desired product as an oil.

Analysis for $C_{25}H_{40}O_5S_2 \cdot \frac{1}{2}H_2O$: Calculated: C, 60.82; H, 8.37; S, 12.99. Found: C, 60,89; H, 8.18; S, 12.86.

EXAMPLE 9

Preparation of 4,6-Dithia-5-[2-(4-(4-butylphenyl)butyl)phenyl]-nonanedioic acid

(a) 2-[4-(4-Butylphenyl)butyl]benzaldehyde

Aluminum chloride (0.23 moles) was added in portions over 7 minutes to a mixture of butylbenzene (0.10 moles) and succinic anhydride (0.11 moles) in ethylene chloride (100 ml), cooled to about 13° C. Thirty minutes later the reaction mixture was poured into ice cold 3N hydrochloric acid (250 ml) and then extracted with ethyl acetate (2×100 ml). The extract was washed with saturated sodium chloride (100 ml), dried over magnesium sulfate and evaporated to give 4-(4-butylphenyl)-4-oxobutanoic acid (mp 107°–111.5° C.). A mixture of this acid (31.63 mmoles), sulfuric acid (0.5 ml) and 10% palladium on charcoal (755 mg) in ethyl acetate (150 ml) was shaken under 50 psi hydrogen for about 15 minutes to yield the reduced product, 4-(4-butylphenyl)butanoic acid (mp 56°–58° C.). A solution of this acid (27.05 mmoles) in sieve dried tetrahydrofuran (25 ml) was reduced with ice cold diborane in tetrahydrofuran (30 mmoles) for about 1.5 hours to give 4-(4-butylphenyl)-butanol as an oil. To an ice cold solution of the butanol (27 mmoles) and carbon tetrabromide (32.56 mmoles) in methylene chloride (50 ml) was added triphenylphosophine (32.75 mmoles) in methylene chloride (50 ml) over 15 minutes. The reaction mixture was stirred for 45 minutes and then the volatiles were evaporated. The resulting oil was triturated with hexane (2×100 ml), filtered, and the filtrate evaporated and chromatographed to leave 4-(4-butylphenyl)butyl bromide as an oil.

Following the procedures of Example 1(a), (b) and (c), to 4-(4-butylphenyl)butylmagnesium bromide (from 21.47 mmoles of 4-(4-butylphenyl)butyl bromide and 18.96 mmoles of magnesium) in distilled tetrahydrofuran (35 ml) was added 2-(2-methoxyphenyl)-4,4-dimethyloxazoline (16.32 mmoles) in tetrahydrofuran (15 ml). Workup of the reaction mixture furnished 2-[2-(4-(4-butylphenyl)butyl)phenyl]-4,4-dimethyloxazoline as an oil. A solution of the oxazoline (14.41 mmoles) in methyl iodide (20 ml) was refluxed under argon for 18 hours. Removal of the volatiles afforded the corresponding 3,4,4-trimethyloxazolinium iodide as a white solid (mp 91°–94° C.). To an ice cold solution of the iodide (14.07 mmoles) in methanol was added in portions sodium borohydride (14.30 mmoles). Similar treatment of the reaction mixture resulted in the isolation of the desired benzaldehyde product as an oil.

Analysis for $C_{21}H_{26}O$: Calculated: C, 85.67; H, 8.90. Found: C, 86.06; Found, 9.19.

(b) 4,6-Dithia-5-[2-(4-(4-butylphenyl)butyl)phenyl]-nonanedioic acid

To an ice cold solution of the aldehyde from Example 9(a) (5.03 mmoles) and 3-mercaptopropionic acid (10.90 mmoles) in methylene chloride (30 ml) was added dropwise boron trifluoride etherate (5.04 mmoles). After 7 minutes the reaction mixture was taken up in ether (100 ml) and washed with water (5×100 ml). Treatment with magnesium sulfate and charcoal, followed by evaporation, left an oil which was purified by flash chromatography (silica gel and 2:1 hexane/ethyl acetate 0.5% formic acid as eluant) to give the desired product.

Analysis for $C_{27}H_{36}O_4S_2 \cdot \frac{3}{4}$ mole ethyl acetate: Calculated: C, 64.95; H, 7.63; S, 11.56. Found: C, 64.74; H, 7.31; S, 11.85.

EXAMPLE 10

Preparation of
4,6-Dithia-5-[2-(1-transdodecenyl)phenyl]-nonanedioic acid

(a) 2-(1-trans-dodecenyl)benzaldehyde

To a suspension of lithium aluminum hydride (22.2 mmoles) in tetrahydrofuran (30 ml) under argon, cooled to 0° C., was added 2-(1-dodecyn-1-yl) benzaldehyde (11.1 mmoles, prepared as in Example 4a) in tetrahydrofuran (10 ml), dropwise with stirring. After coming to room temperature, the reaction mixture was refluxed for 18 hours. The reaction mixture was then cooled to 0° C., ice was added, followed by ether and dilute hydrochloric acid, and the layers were separated. The organic layer was washed with water and brine. The dried solution was concentrated to give 2-(1-transdodecenyl)benzyl alcohol, after recrystallization from acetonitrile. The benzyl alcohol (0.080 mmoles) was dissolved in ethyl acetate (10 ml) under argon and manganese dioxide (12.6 mmoles) was added. The reaction mixture was stirred for 18 hours at room temperature, filtered and the filtrate concentrated to leave an oil which is the desired product.

(b) 4,6-Dithia-5-[2-(1-trans-1-dodecenyl)phenyl]nonanedioic acid

Employing the general method of Example 1(d), the compound of Example 10(a) (0.771 mmoles) was reacted with mercaptopropionic acid (1.7 mmoles) to yield the desired product as a white solid, mp 37°–40° C.

Analysis for $C_{25}H_{38}O_4S_2$: Calculated: C, 64.34; H, 8.21. Found: C, 64.52; H, 8.20.

EXAMPLE 11

Preparation of
4,6-Dithia-5-[2-(11-dodecynyl)phenyl]nonanedioic acid

(a) 2-(11-Dodecynyl)benzaldehyde

To a solution of trimethylsilylacetylene (66.6 mmoles) in tetrahydrofuran (25 ml) cooled to −15° C., under argon, was added dropwise n-butyl lithium (25.6 ml of 2.6 moles in hexane). The resulting solution was stirred for 15 minutes and hexamethylphosphoramide (25 ml) was added. After stirring for 15 minutes the solution was cooled further to −78° C. and decyl dibromide (66.6 mmoles) in tetrahydrofuran (150 ml) was added all at once. The reaction mixture was allowed to warm to room temperature and then poured into ice water/ether. The organic layer was washed with water and saturated sodium chloride solution, dried and concentrated. The residual product was purified by flash chromatography (silica column, eluted with hexane) to give trimethylsilyl 11-dodecynyl bromide. This compound (26.15 mmoles) in tetrahydrofuran (50 ml) was added to magnesium turnings (22.35 mmoles) and to the resulting Grignard reagent was added 2-(2-methoxyphenyl)-4,4-dimethyloxazoline (14.9 mmoles) in tetrahydroduran (30 ml). The solution was stirred under argon at room temperature for 18 hours, cooled and aqueous ammonium chloride was added dropwise. The reaction mixture was diluted with water and ether, and the organic layer was dried and evaporated to leave the product which was purified by flash chromatography to give 2-(trimethylsilyl 11-dodecynylphenyl)-4,4-dimethyloxazoline. A solution of this compound (7.36 mmoles) in methyl iodide (25 ml) was refluxed for 15 hours. The volatiles were removed under vacuum to leave the semi-solid 2-(trimethylsilyl 11-dodecynylphenyl)-3,4,4-trimethyloxazolinium iodide. To a cooled solution (0° C.) of this compound (6.96 mmoles) in methanol (30 ml) was added in portions sodium borohydride (7.30 mmoles). The reaction mixture was stirred for 30 minutes and then quenched with 5% sodium hydroxide solution. The product was extracted into ether and the dried extract was concentrated to leave an oil which was dissolved in acetone (50 ml). Hydrochloric acid (10 ml, 3N) was added and the mixture was stirred at room temperature for 18 hours. The acetone was removed in vacuo and the residue partitioned between water and ether. The organic layer was dried an concentrated to give the product which was purified by flash chromatography to give as an oil, 2-(trimethylsilyl 11-dodecynyl)benzaldehyde. This compound (2.86 mmoles) was dissolved in methanol (10 ml) under argon, and potassium carbonate (100 mg) was added. The mixture was stirred at room temperature for 18 hours and the solvent removed in vacuo. The residue was dissolved in methylene chloride and the solution washed with 5% sodium bicarbonate solution, water and brine. The dried solution was concentrated to give the desired 2-(11-dodecynyl)benzaldehyde as an oil.

(b) 4,6-Dithia-5-[2-(11-dodecynyl)phenyl]nonanedioic acid

Employing the general method of Example 1 (d), the compound of Example 11(a) (2.73 mmoles) was reacted with mercaptopropionic acid (6.01 mmoles) to yield the product as a white solid, mp 34°–38° C.

Analysis for $C_{25}H_{36}O_4S_2$: Calculated: C, 64.62; H, 7.81. Found: C, 64.51; H, 7.80.

EXAMPLE 12

Preparation of
4,6-Dithia-5-[2-(8-phenyloctyl)-5-trifluoromethylphenyl]nonanedioic acid

(a) 2-(8-Phenyloctyl)-5-trifluoromethyl benzaldehyde

To a solution of 2-bromo-5-trifluoromethyl benzonitrile (20.16 mmoles) in methylene chloride (50 ml), under argon at room temperature, was added diisobutylaluminum hydride (25 mmoles, 25 ml hexane) dropwise and the resulting solution was stirred for 30 minutes. The reaction mixture was diluted with ether (50 ml), cooled in ice and quenched by the careful addition of hydrochloric acid (50 ml, 3N). The ice bath was removed and the mixture was stirred vigorously for 15 minutes. The organic layer was washed with brine (50 ml), treated with magnesium sulfate-charcoal and evaporated. The resulting oil was purified by distillation to give 2-bromo-5-trifluoromethyl benzaldehyde, bp 50°–55° C. at 0.05 mm Hg. A mixture of this compound (16.24 mmoles), 1-phenylocta-1,7-diyne (19.54 mmoles, prepared as in Example 7b), cuprous iodide (0.19 mmoles) and bis(triphenylphosphine) palladium chloride (0.34 mmoles) in triethylamine (50 ml) was refluxed under argon for 30 minutes. The reaction mixture was cooled and filtered. The filtrate was evaporated, taken up in ether (100 ml), washed with hydrochloric acid (50 ml, 3N) and sodium chloride, and treated with magnesium sulfate-charcoal. Filtration and evaporation left an oil which was purified by flash chromatography (5% ether/hexane) to yield 2-(8-phenyloctadiyn-1,7-yl)-5-trifluoromethyl benzaldehyde as an oil. A solution of this compound (13.26 mmoles) in ethyl acetate (100 ml) was treated with charcoal for 30 minutes and then filtered. The solution was then shaken under 50 psi of hydrogen with 10% palladium on charcoal (502 mg) for about 90 minutes. Thin layer chromatography of the reaction mixture indicated about 50% reduction of the aldehyde to the alcohol. To re-oxidize the alcohol, the palladium catalyst was filtered off and manganese dioxide (20 g) was added. This mixture was then stirred at room temperature under argon for 18 hours. Filtration and evaporation gave an oil which was purified by flash chromatography (2% ether/hexane) to afford 2-(8-phenyloctyl)-5-trifluoromethyl benzaldehyde as an oil.

(b)
4,6-Dithia-5-[2-(8-phenyloctyl)-5-trifluoromethyl-phenyl]nonanedioic acid

Employing the general method of Example 1(d), the compound of Example 12(a) (2.75 mmoles) was reacted with mercaptopropionic acid (5.97 mmoles) to yield the desired product as a pale yellow liquid. It was converted to the dipotassium salt by dissolving in potassium carbonate solution (15 ml, 0.3M) and isolated by lyophilization.

Analysis for $C_{28}H_{33}F_3O_4S_2K_2$: Calculated: C, 53.14; H, 5.26. Found: C, 52.97; H, 5.29.

Similarly, following the procedures of Example 12(a), and (b), 3-bromobenzaldehyde (5.13 mmoles) was reacted with 1-phenylocta-1,7-diyne (6.04 mmoles) to yield 3-(8-phenyloctadiyn-1,7-yl)benzaldehyde which was reduced/oxidized to 3-(8-phenyloctyl)benzaldehyde and the latter (1.87 mmoles) was reacted with mercaptopropionic acid (4.02 mmoles) to give 4,6-dithia-5-[3-(8-phenyloctyl)phenyl]nonanedioic acid, mp 56°–60° C.

EXAMPLE 13

Preparation of
4,6-Dithia-5-[2-(5-(4-acetyl-3-hydroxy-2-propylphenoxy)-pentoxy)-phenyl]nonanedioic acid (a)
2-[5-(4-acetyl-3-hydroxy-2-propylphenoxy)-pentoxy]-benzaldehyde A solution of salicylaldehyde (82 mmoles) in acetone (50 ml) was added dropwise to a refluxing solution of 1,5-dibromopentane (90.2 mmoles), potassium carbonate (90.2 mmoles) and potassium iodide (0.4 g) in acetone (200 ml). The mixture was refluxed for 18 hours, filtered and the filtrate concentrated. The residue was dissolved in ether and washed with cold 10% sodium hydroxide solution, water and brine. The organic layer was dried over magnesium sulfate and concentrated. The product was purified by flash chromatography (4% ethyl acetate/hexane) to give 2-(5-bromopentoxy)benzaldehyde. A mixture of this compound (11.1 mmoles), 4-acetyl-3-hydroxy-2-propyl phenol (11.62 mmoles) and potassium carbonate (5.55 mmoles) in acetone (30 ml) was refluxed for 5 days, stirred at room temperature for 2 days and then refluxed for 24 hours. The suspension was cooled to room temperature, filtered and the filtrate concentrated. The residue was dissolved in ethyl acetate and then washed with ice-cold 5% sodium hydroxide solution, water and brine. The dried solution was concentrated and the product flash chromatographed on silica gel and eluted with ethylacetate/hexane to give the desired product.

(b)
4,6-Dithia-5-[2-(5-(4-acetyl-3-hydroxy-2-propylphenoxy)-pentoxy)phenyl]nonanedioic acid Employing the general procedure of Example 1(d), the compound of Example 13(a) (2.6 mmoles) was reacted with mercaptopropionic acid (5.2 mmoles) to yield the desired product as a yellow liquid. It was converted to the disodium salt by dissolving in sodium carbonate solution (0.5M) and isolated by lyophilization, mp 146°–148° C. (dec).

Analysis for $C_{29}H_{36}O_8S_2Na_2 3/4H_2O$: Calculated: C, 54.75; H, 5.94; S, 10.08. Found: C, 54.51; H, 5.80; S, 10.12.

EXAMPLE 14

Preparation of
4,6-Dithia-5-[2-(7-phenylthioheptyl)-phenyl]nonanedioic acid (a) 2-(7-Bromoheptyl)benzoic acid Diisopropylamine (61.8 ml, 441 mmoles) was dissolved in tetrahydrofuran (200 ml) and cooled to 0° C. in an ice-methanol bath while stirring under argon. A 2.6M solution of n-butyllithium in hexane (170 ml, 441 mmoles) was added dropwise. Toluic acid (30.0 g, 221 mmoles) was then added and the reaction immediately turned a deep red color. This mixture was added slowly to a solution of 1,6-dibromohexane (84 ml, 551 mmoles) in tetrahydrofuran (200 ml) at 0° C. Following the addition, the ice bath was removed and the reaction mixtue was stirred at room temperature under argon for 18 hours. The solvent was evaporated and the residue dissolved in ether. The ether was extracted with cold 1N sodium hydroxide solution. The pH of the aqueous phase was adjusted to 8.0 with cold concentrated hydrochloric acid and extracted with ether. The ether extract was dried over anhydrous magnesium sulfate, filtered and evaporated to afford the desired product.

(b) 2-(7-Phenylthioheptyl)benzoic acid

The compound of Example 14(a) (2.5 g, 8 mmoles) was dissolved in dimethylformamide (50 ml), to which was added a mixture of thiophenol (1.3 ml, 12.6 mmoles) and triethylamine (4.7 ml, 33 mmoles) in dimethylformamide (50 ml). The reaction mixture was heated to 80° C. for 1-2 hours. The solvents were evaporated and the residue flash chromatographed on silica gel eluted with 15% ethyl acetate in hexane plus 1% formic acid to provide the desired product.

(c) 2-(7-Phenylthioheptyl)benzyl alcohol

To a suspension of lithium aluminum hydride (0.292 g, 7 mmoles) in tetrahydrofuran (30 ml) was added a solution of the compound of Example 14(b) (2.39 g, 7 mmoles) in teterahydrofuran (30 ml). The reaction mixture was stirred at room temperature under argon for 18 hours. Several drops of ice water were added, followed by cold 10% sodium hydroxide solution (1.0 ml) followed by more ice water. The precipitate was filtered and washed, and the filtrate was dried over magesium sulfate, filtered and evaporated. The crude alcohol was flash chromatographed on silica gel with 10% ethyl acetate in hexane to give the desired product.

(d) 2-(7-Phenylthioheptyl)benzaldehyde

To a suspension of manganese dioxide (11.78 g, 135 mmoles) in ethyl acetate (30 ml) was added a solution of the compound of Example 14(c) (11.78 g, 3.7 mmoles) in ethyl acetate (20 ml). The reaction mixture was stirred at room temperature under argon for 1.5 hours. The suspension was filtered, and the filtrate was dried over magnesium sulfate, filtered and evaporated to give the product.

(e) 4,6-Dithia-5-[2-(7-phenylthioheptyl)phenyl]nonanedioic acid

The compound of Example 14(d) was dissolved in methylene chloride (5.0 ml), cooled to 0° C. and mercaptopropionic acid (0.123 ml, 1.3 mmoles) was added, followed by boron trifluoride etherate (0.182 g, 1.3 mmoles). The reaction mixture was stirred under argon for 5-10 minutes. The solvents were evaporated and the residue was dissolved in carbon tetrachloride and washed with water. The organic phase was dried over magnesium sulfate, filtered and evaporated to give the desired product.

Analysis for $C_{26}H_{34}O_4S_3$: Calculated: C, 61.63; H, 6.76; S, 18.98. Found: C, 61.59; H, 6.87; S, 18.90.

Similarly, following the procedures of Example 14(b)-(e), the indicated substituted thiophenols are employed to give the corresponding products:

| Substituted thiophenol | Product |
| --- | --- |
| 4-fluorothiophenol | 4,6-dithia-5-[2-(7-(4-fluorophenylthio)heptyl)phenyl]nonanedioic acid |
| 4-bromothiophenol | 4,6-dithia-5-[2-(7-(4-bromophenylthio)heptyl)phenyl]nonanedioic acid |
| 4-methoxythiophenol | 4,6-dithia-5-[2-(7-(4-methoxyphenylthio)heptyl)phenyl]nonanedioic acid |
| 3-trifluoromethylthiophenol | 4,6-dithia-5-[2-(7-(3-trifluoromethylphenylthio)heptyl)phenyl]nonanedioic acid |
| 4-trifluoromethylthiophenol | 4,6-dithia-5-[2-(7-(4-trifluoromethylphenylthio)heptyl)phenyl]nonanedioic acid |

EXAMPLE 15

Preparation of 4,6-Dithia-5-[2-(8-phenyl-7(Z)-octenyl)phenyl]nonanedioic acid (a) 7-(2-Carboxyphenyl)heptyl-1-triphenylphosphonium bromide To a mixture of the compound of Example 14(a) (10.0 g, 34 mmoles) in toluene (50 ml) was added a solution of triphenylphosphine (9.68 g, 37 mmoles) in toluene (50 ml). The reaction mixture was heated to 80° C. and stirred under argon for 3 days. The separated oil was removed and the solvent evaporated to give the phosphonium bromide.

(b) 2-(8-Phenyl-7(Z)-octenyl)benzoic acid

A mixture of the compound of Example 15(a) (1.4 g, 4.5 mmoles) and tetrahydrofuran (15 ml) under argon was cooled to −78° C. with a dry ice acetone bath. A 26M solution of n-butyllithium in hexane (3.55 ml, 9 mmoles) was added dropwise. The resulting red-orange solution was stirred at −78° C. for 30 minutes. Hexamethylphosphoramide (5.5 ml) was added in one portion followed by benzaldehyde (0.41 ml, 4 mmoles) in tetrahydrofuran (5 ml). The reaction mixture was stirred under argon for 30 minutes. The tetrahydrofuran was evaporated and the residue was dissolved in ether and washed with cold 3N hydrochloric acid. The combined organic phase was dried over magnesium sulfate, filtered and evaporated. The crude material was then chromatographed on silica gel eluted with 4% ethyl acetate in hexane plus 1% formic acid to yield the desired compound.

(c) 4,6-Dithia-5-[2-(8-phenyl-7(Z)-octenyl)phenyl]nonanedioic acid

Employing the procedures of Example 14(c)-(e), the compound of Example 15(b) was reduced with lithium aluminum hydride, the benzyl alcohol was oxidized with manganese dioxide and the benzaldehyde was reacted with mercaptopropionic acid to yield the desired product, whose identity was verified by nuclear magnetic resonance, thin layer chromatography and mass spectra data.

EXAMPLE 16

Preparation of 4,6-Dithia-5-[2-(8-(4-trifluoromethylphenyl)octyl)phenyl]nonanedioic acid (a) 2-[8-(4-trifluoromethylphenyl)-7(Z)-octenyl]benzyl alcohol Employing the procedure of Example 15(b), the compound of Example 15(a) is treated with n-butyllithium followed by 4-trifluoromethylbenzaldehyde to give 2-[8-(4-trifluoromethylphenyl)-7(Z)-octenyl]benzoic acid which is reduced with lithium aluminum hydride to give the desired benzyl alcohol.

(b) 2-[8-(4-Trifluoromethylphenyl)octyl]benzaldehyde

A mixture of methanol (200 ml), 10% palladium on charcoal (3.0 mg) and the compound of Example 16(a) (288.9 mg, 0.8 mmole) was hydrogenated in a Parr bottle until the reaction was complete as determined by nuclear magnetic resonance. The reaction mixture was filtered, washed and the filtrate concentrated to yield 2-[8-(4-trifluoromethylphenyl)octyl]benzyl alcohol. The latter was oxidized, employing the procedure of Example 14(d), with manganese dioxide to give the desired product.

(c) 4,6-Dithia-5-[2-(8-(4-trifluoromethylphenyl)octyl)phenyl]nonanedioic acid

Employing the procedure of Example 14(e), the compound of Example 16(b) was reacted with mercaptopropionic acid to yield the desired product.

Analysis for $C_{28}H_{35}F_3O_4S_2$ 1/2$H_2O$: Calculated: C, 59.45; H, 6.41. Found C, 59,33; H, 6.29.

Similarly, following the procedures of Example 18(a)-(c), the indicated substituted benzaldehydes are employed to give the corresponding products:

| Substituted benzaldehyde | Product |
| --- | --- |
| 4-fluorobenzaldehyde | 4,6-dithia-5-[2-(8-(4-fluorophenyl)octyl)phenyl nonanedioic acid |
| 4-bromobenzaldehyde | 4,6-dithia-5-[2-(8-(4-bromophenyl)octyl)phenyl]nonanedioic acid |
| 4-methoxybenzaldehyde | 4,6-dithia-5-[2-(8-(4- |

| -continued | |
|---|---|
| Substituted benzaldehyde | Product |
| 3-trifluoromethylbenzaldehyde | methoxyphenyl)octyl)-phenyl]nonanedioic acid 4,6-dithia-5-[2-(8-(3-trifluoromethylphenyl)octyl)-phenyl]nonanedioic acid |

EXAMPLE 17

Preparation of
4,6-Dithia-5-[2-(7-(4-fluorophenylthio)heptyl)phenyl]-nonanedioic acid (a) 2-(7-4-fluorophenylthio)benzoic acid The compound of Example 14(a), 2-(7-bromoheptyl)-benzoic acid (0.5 g, 1.68 mm), was reacted with 4-fluorothiophenol (0.322 g., 2.5 mm), and triethylamine (0.94 ml, 6.7 mm) in DMF (30 ml) as in Example 14(b) to afford the desired product. This was further purified by flash chromatography over silica gel with 15% ethyl acetate in hexane.

(b) 2-(7-(4-fluorophenylthio)heptyl)benzyl alcohol

The compound of Example 17(a), (0.495 g., 1.43 mm), was reacted with lithium aluminum hydride (0.057 g., 1.43 mm) in THF (20 ml) as in Example 14(c) to afford the desired product.

(c) 2-(7-(4-fluorophenylthio)heptyl)benzaldehyde

The compound of Example 17(b), (0.213 g., 0.58 mm), was reacted with $MnO_2$ (2.13 g., 24.5 mm) in ethyl acetate (20 ml) as in Example 14(d) to afford the desired product.

(d)
4,6-dithia-5-[2-(7-4-fluorophenylthio)heptyl)phenyl]-phenyl]nonanedioic acid The compound of Example 17(c), (0.202 g., 0.61 mm) was reacted with mercaptopropionic acid (0.107 ml, 1.22 mm) and boron trifluoride etherate (0.174 g., 1.22 mm) in $CH_2Cl_2$ (10 ml) at 0° C. as in Example 14(e) to afford a crude product. This material was flash chromatographed over silica gel with 40% ethyl acetate in hexane with a trace of formic acid to yield the desired product.

Analysis for $C_{26}H_{33}O_4S_3F$: Calculated: C, 59.51; H, 6.34. Found: C, 59.79; H, 6.45.

EXAMPLE 18

Preparation of
4,6-Dithia-5-[2-(7-(4-methoxyphenylthio)heptyl)-phenyl]nonanedioic acid (a) 2-(7-(4-methoxyphenylthio)heptyl)benzoic acid The compound of Example 14(a), 2-(7-bromoheptyl)-benzoic acid (1 g., 3.34 mm) was reacted with 4-methoxybenzenethiol (0.618 ml, 5.03 mm), and triethylamine (1.87 ml, 13.42 mm) in DMF (40 ml) as in Example 14(b) to afford the desired product.

(b) 2-(7-(4-methoxyphenylthio)heptyl)benzyl alcohol

The compound of Example 18(a), (0.542 g., 1.5 mm), was reacted with lithium aluminum hydride (0.061 g., 1.5 mm) in THF (30 ml) as in Example 14(c) to afford the desired product.

(c) 2-(7-(4-methoxyphenylthio)heptyl]benzaldehyde

The compound of Example 18(b), (0.448 g., 1.3 mm), was reacted with $MnO_2$ (4.48 g., 51.5 mm) in ethyl acetate (50 ml) as in Example 14(d) to afford a crude product. This was further purified by flash chromatography over silica gel with ethyl acetate/hexane.

(d)
4,6-dithia-5-[(2-(7-(4-methoxyphenylthio)heptyl)-phenyl]nonanedioic acid

The compound of Example 18(c), (0.354 g., 1.03 mm) was reacted with mercaptopropionic acid (0.18 ml, 2.07 mm) and boron truflioride etherate (0.294 g., 2.07 mm) in $CH_2Cl_2$ (20 ml) at 0° C. as in Example 14(e) to afford the desired product.

Analysis for $C_{27}H_{36}O_5S_3$: Calculated: C, 60.41; H, 6.76. Found C, 58.94; H, 6.62.

EXAMPLE 19

Preparation of
4,6-Dithia-5-[2-(7-(4-bromophenylthio)heptyl)phenyl]-nonanedioic acid (a) 2-(7-(4-bromophenylthio)heptylbenzoic acid The compound of Example 14(a), 2-(7-bromoheptyl)-benzoic acid (0.6 g., 2.01 mm), was reacted with 4-bromothiophenol (0.60 g., 3 mm), and triethylamine (1.12 ml, 8.05 mm) in DMF (35 ml) as in Example 14(b) to afford the desired product. This was further purified by flash chromatography over silica gel with ethyl acetate in hexane.

(b) 2-(7-(4-bromophenylthio)heptyl)benzyl alcohol

The compound of Example 19(a), (0.49 g., 1.2 mm), was reacted with lithium aluminum hydride (0.048 g., 1.2 mm) in THF (20 ml) as in Example 14(c) to afford the desired product.

(c) 2-(7-(4-bromophenylthio)heptyl)benzaldehyde

The compound of Example 19(c), (0.324 g., 0.83 mm) was reacted with mercaptopropionic acid (0.144 ml, 1.66 mm) and boron trifluoride etherate (0.235 g., 1.66 mm) in $CH_2Cl_2$ (15 ml) at 0° C. as in Example 14(e) to afford the desired product.

Analysis for $C_{26}H_{33}O_4S_3Br$: Calculated C, 53.32; H, 5.68. Found: C, 52.98; H, 5.71.

EXAMPLE 20

Preparation of
4,6-Dithia-5-(2-undecyloxy-5-bromophenyl)nonanedioic acid (a) 2-Undecyloxy-5-bromo benzaldehyde 5-Bromosalicylaldehyde (1.51 g, 7.5 mm) was dissolved in dry DMF and treated with sodium hydride (0.4 g, 8.3 mm, 50% dispersion). After stirring for 20 minutes, a solution of 1-bromo-undecane in DMF was added dropwise. The reaction was heated to 50°–65° C. overnight with stirring. The reaction was then poured into ice water, the pH was adjusted to 8.0 with $K_2CO_3$ and the mixture was extracted with diethylether. The organic extracts were washed with water, dried over $MgSO_4$ and filtered. The solvent was evaporated to yield an oil which solidifies upon standing.

(b) 4,6-Dithia-5-(2-undecyloxy, 5-bromophenyl)nonanedioic acid

The compound of example 20(a), (1.14 g, 3.2 mm) was reacted with 3-mercaptoproprionic acid (0.742 g, 7 mm) and boron trifluoride etherate (0.45 ml, 3.2 mm) in methylene chloride at 0° C. as in example 14(c) to afford a crude product. This material was triturated with petroleum ether, filtered and dried under high vaccum to yield a solid which melted at 79°–81° C.

Analysis for $C_{24}H_{36}BrO_5S_2$: Calculated: C, 52.55; H, 6.61. Found: C, 52.40; H, 6.73.

EXAMPLE 21

Preparation of 4,6-Dithia-5-(2-undecyloxy-5-nitrophenyl)nonanedioic acid

(a) 2-Undecyloxy-5-nitrobenzaldehyde

5-Nitrosalicylaldehyde (1.7 g, 10 mm) was dissolved in 20 ml dry DMF and $K_2CO_3$ (2.2 g, 16 mm) was added cautiously. The reaction was stirred at room temperature for 20 minutes and 1-bromoundecane (2.6 g, 11 mm), in 20 ml dry DMF, was added dropwise to the mixture. The reaction was heated at 89° C. for 3 days, cooled and poured into 100 ml $H_2O$. The product was extracted with diethyl ether, washed with 5% aqueous $Na_2CO_3$ and brine, and dried over $MgSO_4$. Filtration and evaporation of the solvent yielded an oil which was chromatographed over silica gel using 10% ethylacetate/hexane. This yielded an oil which crystallized upon scratching. The resulting white solid melted at 47°–48° C.

(b) 4,6-Dithia-5-(2-undecyloxy-5-bromophenyl)nonanedioic acid

The compound in Example 21(a), (1.3 g, 4 mm) was dissolved in 3-mercaptopropionic acid (10 g, 90 mm) and, with stirring, gaseous hydrochloric acid was bubbled through the solution for a few seconds. The reaction mixture was stirred at room temperature for 15 minutes and poured into 100 ml $H_2O$. After stirring for 1 hour the precipitated white solid was collected by filtration and washed with water. The solid was dissolved in methylene chloride, and this solution was washed with water and dried over $MgSO_4$. Filtration and evaporation of the solvent yielded the desired product as a white solid which melted at 99°–100° C.

Analysis for $C_{24}H_{37}NO_7S_2$: Calculated: C, 55.89; H, 7.23; N, 2.72. Found: C, 55.96; H, 7.31; N, 2.79.

EXAMPLE 22

As a specific embodiment of a composition useful in the method of this invention, an active ingredient, such as the compound of Example 1(d), is dissolved in 25 mM sodium carbonate at a concentration of 0.4 percent and aerosolized from a nebulizer oper

4. A method of claim 2 comprising administration of a compound which is 4,6-dithia-5-[3-(8-phenyloctyl)-phenyl]nonanedioic acid.

5. A method of claim 2 comprising administration of a compound which is 4,6-dithia-5-[2-(10-phenyldecyl)-phenyl]nonanedioic acid.

6. A method of claim 2 comprising administration of a compound which is 4,6-dithia-5-[2-(8-phenyloctyl)-4-trifluoromethylphenyl]nonanedioic acid.

7. A method of claim 2 comprising administration of a compound wherein $R_3$ is an alkoxy radical containing 7 to 12 carbon atoms.

8. A method of claim 7 comprising administration of a compound which is 4,6-dithia-5-(5-bromo-2-undecyloxyphenyl)nonanedioic acid.

9. A method of claim 7 comprising administration of a compound which is 4,6-dithia-5-(2-undecyloxy-5-nitrophenyl)nonanedioic acid.

10. A method of claim 2 comprising administration of a compound wherein $R_3$ is a phenyl-$C_4$ to $C_{10}$ alkyl radical with the phenyl optionally mono substituted with bromo, chloro, trifluoromethyl, methoxy, methylthio or trifluoromethylthio, phenylthio-$C_3$ to $C_9$ alkyl radical with the phenyl optionally mono substituted with bromo, chloro, trifluoromethyl, methoxy, methylthio, fluoro or trifluoromethylthio, or phenyl-$C_3$ to $C_9$ alkoxy radical.

11. A method of claim 10 comprising administration of a compound which is 4,6-dithia-5-[2-(7-[4-methoxyphenylthio]heptyl)phenyl]nonanedioic acid.

12. A method of claim 10 comprising administration of a comound which is 4,6-dithia-5-[2-(7-(4-fluorophenylthio)heptyl) phenyl]nonanedioic acid.

13. A method of claim 10 comprising administration of a compound which is 4,6-dithia-5-[2-(7-(4-bromophenylthio)heptyl)phenyl]nonanedioic acid.

14. A method of claim 1 comprising administration of a compound represented by the following structural formula (IV):

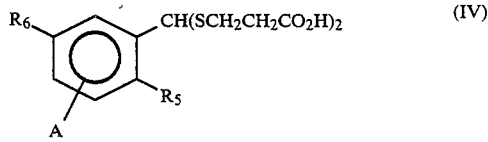

wherein $R_5$ and A are hydrogen and $R_6$ is selected from the group consisting of $(S)_a$—$(CH_2)_b$—$(T)_c$—B wherein a is 0 or 1;

b is 5 to 12;

c is 0 or 1;

S and T are independently sulfur, oxygen, or $CH_2$; and

B is $C_{1-4}$alkyl, ethynyl, trifluoromethyl, or phenyl optionally monosubstituted with Br, Cl, $CF_3$, F, $C_{1-4}$alkoxy, $C_{1-4}$alkyl, methylthio, or trifluoromethylthio.

15. A method of claim 1 comprising administration of a pharmaceutical composition of a pharmaceutical carrier or diluent and a sufficient amount of a compound of formula (I) to inhibit the effects of leukotriene $B_4$.

16. A method of claim 15 comprising administration of a pharmaceutical composition in the form of an aerosol formulation or a sterile solution, or in a form suitable for administration by suppositories, inhalation, parenteral administration or topical administration.

* * * * *